(12) United States Patent
Heida

(10) Patent No.: US 7,692,053 B2
(45) Date of Patent: Apr. 6, 2010

(54) PROCESS FOR OBTAINING CRUDE 1,3-BUTADIENE FROM A $C_4$ CUT

(75) Inventor: Bernd Heida, Ellerstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 770 days.

(21) Appl. No.: 10/585,856

(22) PCT Filed: Feb. 4, 2005

(86) PCT No.: PCT/EP2005/001152

§ 371 (c)(1),
(2), (4) Date: Jul. 12, 2006

(87) PCT Pub. No.: WO2005/075388

PCT Pub. Date: Aug. 18, 2005

(65) Prior Publication Data

US 2008/0228019 A1   Sep. 18, 2008

(30) Foreign Application Priority Data

Feb. 6, 2004   (DE) .................. 10 2004 005 930

(51) Int. Cl.
C07C 7/08 (2006.01)
C07C 11/167 (2006.01)
B01D 3/40 (2006.01)
B01D 3/42 (2006.01)

(52) U.S. Cl. .............. 585/324; 203/1; 203/22; 203/57; 203/DIG. 8; 585/503; 585/615; 585/833; 585/864; 585/911

(58) Field of Classification Search .......... 203/1, 203/21, 22, 52–54, 56–58, 60, 62–63, DIG. 8; 585/324, 501, 503, 615, 833, 864–868, 911
See application file for complete search history.

(56) References Cited

U.S. PATENT DOCUMENTS

| 3,620,930 | A  | * | 11/1971 | Tschopp et al. ........... 203/87 |
| 4,162,198 | A  | * | 7/1979 | Stockburger et al. ........ 203/23 |
| 6,846,966 | B2 | * | 1/2005 | Lumgair et al. ........... 585/639 |
| 7,132,038 | B2 | * | 11/2006 | Bohner et al. ............. 203/1 |
| 2003/0181772 | A1 | | 9/2003 | Meyer et al. |

FOREIGN PATENT DOCUMENTS

| DE | 27 24 365 | 11/1978 |
| DE | 101 05 660 | 8/2002 |
| DE | 103 22 655 | 12/2004 |
| WO | 02/062733 | 8/2002 |
| WO | 2004/011407 | 2/2004 |

* cited by examiner

Primary Examiner—Virginia Manoharan
(74) Attorney, Agent, or Firm—Oblon, Spivak, McClelland, Maier & Neustadt, L.L.P.

(57) ABSTRACT

1,3-butadiene is obtained by extractive distillation with a selective solvent from a $C_4$ cut comprising $C_4$ acetylenes as secondary components in a dividing wall column having a bottom evaporator, in which a dividing wall is disposed in the longitudinal direction of the column to form a first subregion, a second subregion and a lower combined column region. The column is disposed upstream of an extractive wash column. The energy input into the dividing wall column via the bottom evaporator is controlled in such a way that a bottom stream containing solvent, $C_4$ acetylenes and 1,3-butadiene restricted such that the loss of 1,3-butadiene is economically acceptable, is drawn off and fed to an acetylenes outgasser where the $C_4$ acetylenes are stripped out overhead and purified solvent is obtained as the bottom stream.

11 Claims, 1 Drawing Sheet

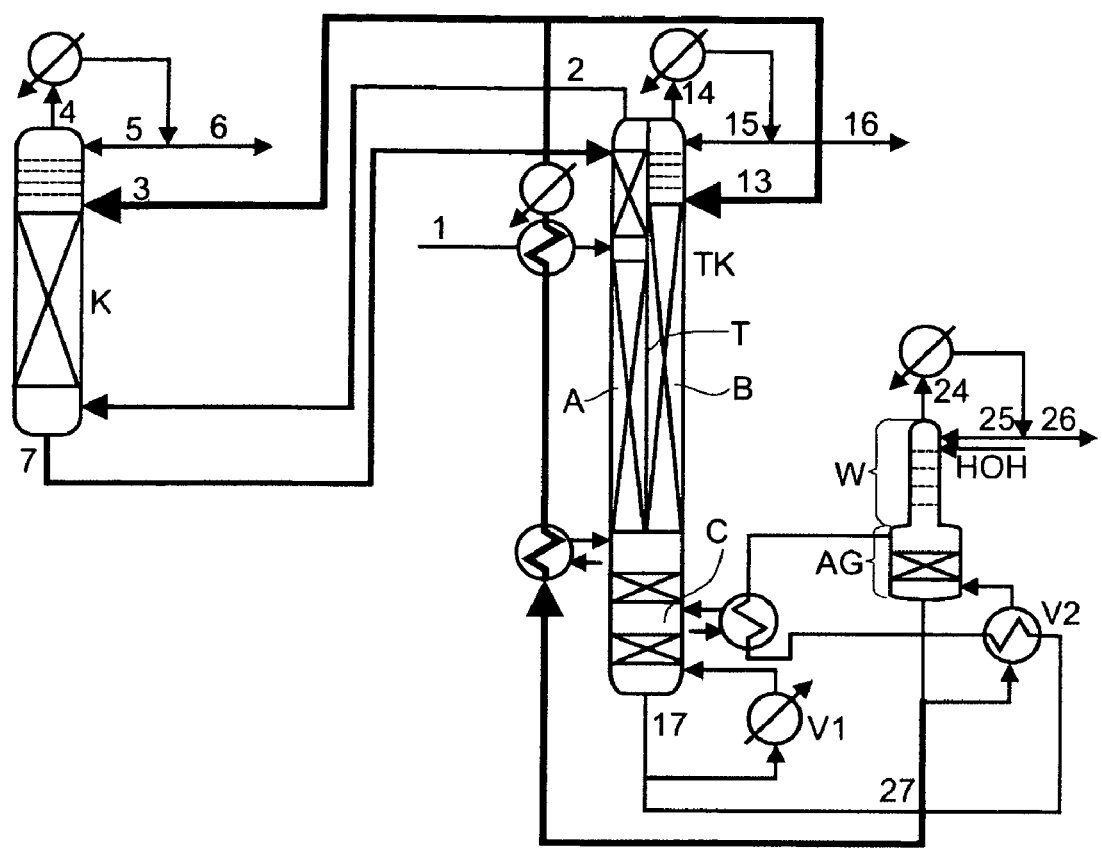

PROCESS FOR OBTAINING CRUDE 1,3-BUTADIENE FROM A $C_4$ CUT

CROSS REFERENCE TO RELATED APPLICATIONS

This application is the National Stage of PCT/EP05/01152, filed Feb. 4, 2005, the disclosure of which is incorporated herein by reference in its entirety. The parent application claims priority to German Application No.102004005930.6, filed Feb. 6, 2004, the disclosure of which is incorporated herein by reference in its entirety.

The invention relates to a process for obtaining crude 1,3-butadiene by extractive distillation with a selective solvent from a $C_4$ cut comprising $C_4$ acetylenes as secondary components in a dividing wall column or in thermally coupled columns.

BACKGROUND OF THE INVENTION

Owing to the small differences in the relative volatilities of the components of the $C_4$ cut, obtaining 1,3-butadiene from a $C_4$ cut is a complicated distillation problem. Therefore, the separation is carried out by extractive distillation, i.e. a distillation with addition of an extractant which has a higher boiling point than the mixture to be separated and which increases the differences in the relative volatilities of the components to be separated. The use of suitable extractants allows a crude 1,3-butadiene fraction to be obtained from the $C_4$ cut mentioned by means of extractive distillation, and said fraction is subsequently further purified in purifying distillation columns.

In the present context, crude 1,3-butadiene refers to a hydrocarbon mixture which has been obtained from a $C_4$ cut from which at least 90% by weight of the sum of butanes and butenes, preferably at least 98% by weight of the sum of butanes and butenes, more preferably at least 99% by weight of the sum of butanes and butenes, and simultaneously at least 90% by weight of the $C_4$ acetylenes, preferably at least 96% by weight of the $C_4$ acetylenes, more preferably at least 99% by weight of the $C_4$ acetylenes, has been removed. Crude 1,3-butadiene contains the 1,3-butadiene product of value frequently in a proportion of at least 80% by weight, preferably 90% by weight, more preferably more than 95% by weight, remainder impurities.

Accordingly, pure 1,3-butadiene refers to a hydrocarbon mixture which contains the 1,3-butadiene product of value in a proportion of at least 98% by weight, preferably of at least 99.5% by weight, more preferably in the range between 99.7 and 99.9% by weight, remainder impurities.

DE-A 101 05 660 discloses a process having simplified constructional design of the apparatus compared to prior processes: the $C_4$ cut is separated in a dividing wall column having a dividing wall extending up to the upper end of the dividing wall column and an extractive wash column upstream of the dividing wall column. According to the process of DE-A 101 05 660, a semidegassed solvent stream is drawn off from the bottom of the dividing wall column used for the extractive distillation. The term "semi-degassed solvent" is familiar to those skilled in the art who work in extractive distillation to obtain 1,3-butadiene and refers to a selective solvent which still contains dissolved components from the $C_4$ cut to be separated, specifically the components which have the greatest affinity for the selective solvent. These include in particular the $C_4$ acetylenes, in particular ethylacetylene and vinylacetylene.

However, a solvent stream which has merely been semidegassed cannot be recycled into the extractive distillation, since the acetylenes damaging to the specification would otherwise accumulate. It was therefore necessary to feed the bottom stream drawn off from the dividing wall column, before the recycling into the extractive distillation, initially to an outgasser column, as disclosed, for example, by DE-A 27 24 365, which is operated at lower pressure compared to the column from whose bottom the semidegassed stream is drawn off. In the outgasser column, the semidegassed solvent stream is processed to obtain a purified, i.e. fully degassed, solvent at the bottom and a gaseous hydrocarbon stream at the top of the outgasser column, which is recycled via a compressor into the lower region of the extractive distillation column. The acetylenes are discharged via a sidestream.

However, according to the process of DE-A 27 24 365, the bottom stream which is drawn off from the dividing wall column and is fed to the outgasser column contains, in addition to the $C_4$ acetylenes, also considerable amounts of the 1,3-butadiene product of value. The 1,3-butadiene goes into the top stream of the outgasser column, which, in an economic operating mode, cannot be discarded, but rather is recycled via a compressor into extractive distillation which is operated at higher pressure compared to the outgasser. The compressor has high energy consumption; the process of DE-A 27 24 365 was therefore actually an advance over prior processes, in which compressors having triple the energy consumption were required. However, at the application date of DE-A 27 24 365, it was unknown to those skilled in the art that a process version which can fully dispense with the compressor can be realized in a technically simple manner.

DE-A 103 22 655 describes a process in which the control of the energy input into the dividing wall column via the bottom evaporator thereof and the configuration of the number of theoretical plates in the lower combined column region can be used to adjust the operation of the dividing wall column in such a way that a bottom stream can be removed from the dividing wall column and already contains purified solvent.

Accordingly, both the outgasser column and the compressor for recycling 1,3-butadiene-containing stream into the extractive distillation become unnecessary.

In the present context, the term purified solvent or fully degassed solvent refers to a solvent which has been depleted in components from the $C_4$ cut to such an extent that it is suitable for use as a selective solvent for the extractive distillation of a $C_4$ cut, while the predefined specifications for crude 1,3-butadiene and raffinate 1 are complied with. Key components in this context are $C_4$ acetylenes, especially ethylacetylene and vinylacetylene.

BRIEF DESCRIPTION OF THE DRAWING

The FIGURE shows one embodiment of the claimed invention.

DETAILED DESCRIPTION OF THE PREFERRED EMBODIMENTS

Accordingly, it is an object of the invention to provide an improved process for the extractive distillation of 1,3-butadiene in compressorless operation, which in particular ensures less fouling in the columns, increased operational reliability and economic viability. Accordingly, a process has been found for obtaining crude 1,3-butadiene by extractive distillation with a selective solvent from a $C_4$ cut comprising $C_4$ acetylenes as secondary components, said process being carried out in a dividing wall column having a bottom evaporator, in which a dividing wall is disposed in the longitudinal direction of the column to form a first subregion, a second subregion and a lower combined column region, and which is disposed upstream of an extractive wash column, which comprises controlling the energy input into the dividing wall column via the bottom evaporator in such a way that a bottom stream is drawn off from the dividing wall column and comprises solvent laden with the $C_4$ acetylenes whose proportion of 1,3-butadiene is restricted such that the loss of 1,3-butadiene is economically acceptable, and feeding the bottom stream to an acetylenes outgasser and, in the acetylenes outgasser, stripping out the $C_4$ acetylenes overhead and obtaining purified solvent as the bottom stream.

It has been found that it is possible to remove the predominant proportion of the hydrocarbons from the $C_4$ cut in the dividing wall column, so that substantially only the hydrocarbons having the best solubility therein, i.e. the $C_4$ acetylenes, remain in the selective solvent. Therefore, it is necessary merely to remove the $C_4$ acetylenes from the bottom stream of the dividing wall column to obtain a purified solvent which is advantageously recycled into the extractive distillation. Since the 1,3-butadiene content in the bottom stream of the extractive distillation column can be reduced to low values, it is economically justifiable not to recycle it back into the extractive distillation, with energy-intensive use of a compressor.

The $C_4$ cut to be used in the present context as a starting mixture is a mixture of hydrocarbons having predominantly four carbon atoms per molecule. $C_4$ cuts are obtained, for example, in the preparation of ethylene and/or propylene by thermal cracking of a petroleum fraction such as liquefied petroleum gas, light petroleum or gas oil. $C_4$ cuts are also obtained in the catalytic dehydrogenation of n-butane and/or n-butene. In general, $C_4$ cuts comprise butanes, n-butene, isobutene, 1,3-butadiene, and additionally small amounts of $C_3$ and $C_5$ hydrocarbons, and also butynes, especially 1-butyne (ethylacetylene) and butenyne (vinylacetylene). The 1,3-butadiene content is generally from 10 to 80% by weight, preferably from 20 to 70% by weight, in particular from 30 to 60% by weight, while the content of vinylacetylene and ethylacetylene generally does not exceed 5% by weight.

Useful extractants, i.e. selective solvents, for the extractive distillation already defined at the outset in the present separation problem, obtaining 1,3-butadiene from the $C_4$ cut, are generally substances or mixtures which have a higher boiling point than the mixture to be separated, and also a greater affinity for conjugated double bonds and triple bonds than for simple double bonds or single bonds, preferably dipolar, more preferably dipolar-aprotic solvents. For apparatus reasons, preference is given to substances having low corrosivity, if any.

Suitable selective solvents for the process according to the invention are, for example, butyrolactone, nitriles such as acetonitrile, propionitrile, methoxypropiononitrile, ketones such as acetone, furfurol, N-alkyl-substituted lower aliphatic amides such as dimethylformamide, diethylformamide, dimethylacetamide, diethylacetamide, N-formylmorpholine, N-alkyl-substituted amides (lactams) such as N-alkylpyrrolidones, especially N-methylpyrrolidone. In general, N-alkyl-substituted lower aliphatic amides or N-alkyl-substituted cyclic amides are used. Dimethylformamide, acetonitrile, furfurol and especially N-methylpyrrolidone are particularly advantageous.

However, it is also possible to use mixtures of these solvents with one another, for example of N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n- or isobutyl tert-butyl ether. N-Methylpyrrolidone, abbreviated in the present context as NMP, is particularly suitable, preferably in aqueous solution, in particular with from 7 to 10% by weight of water, more preferably with 8.3% by weight of water.

The extractive distillation is carried out in a dividing wall column in which a dividing wall is arranged in the longitudinal direction of the column to form a first subregion, a second subregion and a lower combined column region and is connected to an upstream extractive wash column.

Dividing wall columns are used in a known manner for more complex separation tasks, generally for mixtures of at least three components, in which the individual components are each to be obtained in pure form. They have a dividing wall, i.e. generally a flat metal sheet which is aligned in the longitudinal direction of the column and prevents backmixing of the liquid and vapor streams in subregions of the column.

In the present context, a dividing wall column having a special configuration is used, whose dividing wall is extended up to the uppermost point of the column and thus permits mixing of liquid and vapor streams only in the lower combined column region. The first and second subregions are separated from one another by the dividing wall.

In the manner known to those skilled in the art, the dividing wall column may be replaced by appropriately connected thermally coupled columns.

The extractive wash column is a countercurrent wash column. In all columns, there are no restrictions relating to the separating internals which can be used; for reasons of cost, preference is given to random packings.

The acetylenes outgasser is a stripping column; the bottom stream laden with $C_4$ acetylenes from the extractive distillation is applied in the upper region of the acetylenes outgasser and the $C_4$ acetylenes are outgassed in countercurrent with the rising hot gas stream.

To the acetylenes outgasser is preferably attached a water scrubber, in which solvent residues from the outgassed acetylenes stream are washed out with reflux and fresh water. The water scrubber is preferably dimensioned with significantly lower diameter compared to the acetylenes outgasser. At the top of the water scrubber, a stream comprising the $C_4$ acetylenes is obtained and is condensed and partly applied back to the water scrubber as reflux, and otherwise discharged from the process, in particular fed to a cracker or incinerated.

The bottom stream from the acetylenes degasser comprises purified solvent and is preferably recycled into the extractive distillation.

In a preferred process version, the $C_4$ cut is fed to the first subregion of the dividing wall column, preferably into its middle region, the top stream from the first subregion of the dividing wall column is fed to the extractive wash column, into its lower region, in the extractive wash column, a countercurrent extraction is carried out by charging with a first substream of the selective solvent in the upper region of the extractive wash column, the components of the $C_4$ cuts having lower solubility than 1,3-butadiene in the selective solvent are drawn off via the top of the extractive wash column, the bottom stream from the extractive wash column is recycled into the upper region of the first subregion of the dividing wall column, a second substream of the selective solvent is fed to the dividing wall column in the upper region of the second subregion, the top product from the second subregion (B) of the dividing wall column is drawn off as crude 1,3-butadiene and a bottom stream consisting of solvent laden with the $C_4$ acetylenes, whose proportion of 1,3-butadiene is restricted such that the loss of 1,3-butadiene is economically acceptable, is drawn off from the lower combined column region of the dividing wall column, the bottom stream (17) is fed to the acetylenes outgasser (AG) in which the $C_4$ acetylenes are stripped out overhead and purified solvent is obtained as the bottom stream (27) and is recycled into the process.

Preference is thus given to feeding the $C_4$ cut to be separated to the first subregion of the dividing wall column, more preferably into the middle region thereof;

feeding the top stream from the first subregion of the dividing wall column to the upstream extractive wash column into the lower region thereof, carrying out a countercurrent extraction in the extractive wash column by charging with a first substream of the selective solvent in the upper region of the extractive wash column, drawing off the components of the $C_4$ cut which have a lower solubility than 1,3-butadiene in the selective solvent via the top of the extractive wash column, more preferably in a condenser at the top of the extractive wash column, and partly applying it as reflux back to the extractive wash column, otherwise drawing it off as a by-product comprising predominantly butanes and butenes, frequently also referred to as raffinate 1.

The feeding of the bottom stream of the extractive wash column, i.e. of a stream which comprises, in addition to the selective solvent, 1,3-butadiene, butanes, butenes and the components of the $C_4$ cut having better solubility than 1,3-butadiene in the selective solvent, into the upper region of the first subregion of the dividing wall column, by virtue of mass transfer between this stream and the $C_4$ cut applied in vapor form in the upper region of the first subregion of the dividing wall column, allows a countercurrent extraction to be effected with depletion of the components having lower solubility in the selective solvent than 1,3-butadiene at the top of the first subregion of the dividing wall column.

At the lower end of the dividing wall column a vaporous stream is obtained which, in addition to 1,3-butadiene, comprises the components of the $C_4$ cut, especially $C_4$ acetylenes, which have better solubility in the selective solvent than 1,3-butadiene. These are washed out of the rising vaporous stream in countercurrent with a second substream of the selective solvent which is applied in the upper region of the second subregion of the dividing wall column. The vaporous top product from the second subregion of the dividing wall column is drawn off, preferably by condensing it in a condenser at the top of the column, a substream of the condensed top stream is introduced as reflux back to the subregion B of the dividing wall column and the condensed top stream is otherwise drawn off as crude 1,3-butadiene.

In the lower combined column region, the solvent is degassed to obtain, at the bottom of the extractive distillation column, a solvent which comprises the $C_4$ acetylenes and 1,3-butadiene in a proportion whose loss is economically acceptable.

In the determination of the input energy required for this purpose via the bottom evaporator of the extractive distillation column, the process engineer will take into account the thermal stressability of the substance or of the substance mixture which has been used as the selective solvent in each specific case.

When it is permitted by the thermal stressability of the selective solvent, the temperature in the bottom of the extractive distillation column is advantageously set sufficiently high that it is still possible to condense at the top of the extractive distillation column with inexpensive coolants, for example with river water.

However, when the thermal stressability of the selective solvent used in the specific case is not sufficient at the temperature that would be necessary to obtain solvent at the bottom, whose proportion of 1,3-butadiene is restricted such that the loss of 1,3-butadiene is economically acceptable, it is necessary to work at a temperature at the bottom of the column which is still permissible for the selective solvent and accordingly to cool at the top of the column with a more expensive coolant than river water.

A particularly preferred selective solvent is, as detailed above, NMP, preferably in aqueous solution, in particular with from 7 to 10% by weight of water, more preferably with 8.3% by weight of water.

Under the prerequisite that NMP is used as the selective solvent, the temperature in the bottom evaporator of the extractive distillation column is preferably set within the range between 150 and 210° C., more preferably at 178° C. Accordingly, the top pressure in the second subregion of the extractive distillation column configured as a dividing wall column is set within the range from 1 to 10 bar absolute, preferably from 2 to 5 bar absolute, more preferably at 3.5 bar absolute. Preference is given to operating the acetylenes outgasser at a top pressure in the range from 1 bar absolute up to a maximum of the top pressure in the dividing wall column (TK).

It is in principle unnecessary to provide the recovery of the by-product composed of butanes and butenes, known as raffinate 1, in an upstream extractive wash column separate from the extractive distillation column. It is also possible to integrate the extractive wash column into the first subregion of the dividing wall column used as an extractive distillation column, when it is technically and economically realizable taking into account the specific boundary conditions for the process, especially the composition of the $C_4$ cut to be separated and the specification for raffinate 1, in order to appropriately increase the number of theoretical plates in the first subregion of the dividing wall column.

The preferred process variants described hereinbelow, from the process of DE-A 101 05 660 are also equally applicable to the process of the present invention:

In a preferred process variant, the vapor stream at the lower end of the dividing wall of the dividing wall column is divided by means of suitable measures so that the substream conveyed to the first subregion of the dividing wall column is larger than the substream conveyed to the second subregion of the dividing wall column. Regulation of the division of the stream of vapor at the lower end of the dividing wall enables the necessary product specification of the crude 1,3-butadiene stream taken off at the top of the second subregion of the dividing wall column to be ensured in a simple and reliable manner.

Such unequal division of the stream vapor at the lower end of the dividing wall is particularly preferably achieved by the dividing wall being arranged noncentrally so that the second subregion is smaller than the first subregion of the dividing wall column.

The dividing wall is particularly preferably arranged noncentrally so that the cross-sectional ratio of the first subregion to the second subregion is in the range from 8:1 to 1.5:1, in particular 2.3:1.

As an alternative to or in addition to the noncentral arrangement of the dividing wall, the stream of vapor at the lower end of the dividing wall can be divided in the desired ratio between the two subregions of the dividing wall column by means of further measures, for example flaps or guide plates.

A further additional or alternative measure for division of the stream of vapor at the lower end of the dividing wall is setting of the heat removal power of the condenser at the top of the second subregion of the dividing wall column.

In a preferred process variant, the pressures at the upper end of the two subregions of the dividing wall column can each be regulated separately. This enables the necessary product specification of the crude 1,3-butadiene to be ensured.

The pressures at the top of the two subregions of the dividing wall column are preferably each set by means of a split-range control. The term split-range control refers, in a well-known manner, to an arrangement in which the outlet of the pressure regulator is connected simultaneously to the inert gas line and the venting line. The valve setting range of the pressure regulator is divided so that only one valve is actuated at one time, i.e. either inert gas flows in or venting occurs. This enables the amount of inert gas and the product losses associated with the waste air stream to be minimized.

In addition to or as an alternative to split-range control, it is possible to regulate each of the pressures at the top of the two subregions of the dividing wall column by means of the heat removal power of the condensers at the top of the second subregion of the dividing wall column and at the top of the extractive wash column.

In a preferred variant, it is possible to integrate the acetylenes outgasser by construction into the lower region of the dividing wall column. For this purpose, the number of theoretical plates has to be appropriately increased in the lower combined column region of the dividing wall column and, at the point which corresponds to the upper end of the acetylenes outgasser, a gastight division has to be provided in the dividing wall column, although it is appropriate to ensure a liquid connection, for example by drawing off the liquid above the division and feeding it back below the division.

The heat content of the bottom stream from the extractive distillation column may advantageously be utilized for heat integration in the process itself, especially for heating by indirect heat transfer to the bottom stream drawn off from the acetylenes outgasser and/or to the liquid which is drawn off from one or more separating stages of the dividing wall column, heated and/or evaporated by indirect heat exchange with the hot bottom stream, and recycled back into the lower combined column region of the dividing wall column, and the separating stage(s) is/are advantageously selected in such a way that the total energy requirement for the extractive distillation column is minimal.

Additionally or alternatively, the heat content of the bottom stream of the purified solvent from the acetylenes outgasser may be utilized for indirect heat transfer to the liquid which is drawn off from one or more suitable separation stages in the lower combined column region of the extractive distillation column heated, and/or evaporated and fed back to the extractive distillation column, and/or for heat transfer by indirect heat exchange with the $C_4$ cut to be fed to the extractive distillation column.

It has been found that the heat integration in the present process, owing to the substantially steeper fall in the heat profile in the extractive distillation column, viewed from the bottom evaporator via the lowermost separation stages of the extractive distillation column, is more favorable compared to existing processes, especially compared to the process of DE-A 103 22 655, especially by about 10% compared to said process.

In the present process, the special operating mode of the extractive distillation column in which the $C_4$ acetylenes removal is carried out in an apparatus or apparatus part separated therefrom ensures increased operational reliability, since the risk of acetylenes accumulation beyond their decomposition limit is ruled out.

In addition, the special operating mode achieves a surprisingly advantageous temperature profile in the dividing wall column: even though the bottom evaporator of the dividing wall column is operated only at slightly reduced temperature compared to the existing process, no temperature critical for fouling, i.e. no temperature of generally>150° C., is achieved in the present process in all columns, especially also in the dividing wall column and the acetylenes outgasser. In contrast, the temperature in the region in which the acetylenes are outgassed is distinctly reduced, by about 30-40° C., compared to the existing process, especially with the consequence that substantially less fouling thus arises.

The invention is illustrated in detail hereinbelow with reference to a drawing and a working example:

FIG. 1 shows the scheme of a plant of the invention.

In a dividing wall column TK with a dividing wall T disposed in the longitudinal direction of the column, which divides the dividing wall column into a first subregion A, a second subregion B and a lower combined column region C, a $C_4$ cut 1 is fed to the first subregion A. For example, the second subregion B contains 40 theoretical plates and the lower combined column region C 10 theoretical plates. The top stream 2 from the subregion A is passed into the lower region of the upstream extractive wash column K having, for example, 20 theoretical plates. The extractive wash column K is charged with a first solvent substream 3, into the upper region thereof, and countercurrent extraction occurs, resulting in a bottom stream 7 which is conducted back into the upper region of the subregion A of the dividing wall column TK and a top stream 4 which is condensed in a condenser at the top of the extractive wash column K, and a substream of the condensate is applied again as stream 5 to the extractive wash column K and the condensate is otherwise drawn off as stream 6.

The dividing wall column TK is charged in its second subregion B with a second solvent substream 13. From the second subregion B, a top stream 14 is drawn off and condensed, a substream 15 of the condensed top stream 14 is introduced as reflux to the second subregion B of the dividing wall column and the condensed top stream 14 is otherwise drawn off as crude 1,3-butadiene (stream 16).

From the bottom of the dividing wall column (TK), energy is supplied externally to the plant via the bottom evaporator (V1) of the dividing wall column (TK). Suitable heat integration within the process preferably allows energy to be supplied to the plant externally exclusively at this point.

The bottom stream 17, solvent laden with the $C_4$ acetylenes, whose 1,3-butadiene content does not exceed an upper limit whose loss is economically acceptable, is, preferably after heat integration with the bottom stream from the acetylenes outgasser (AG) and more preferably with the liquid which is drawn off from the lower combined column region (C) of the dividing wall column (TK), fed to the acetylenes outgasser (AG) in the upper region thereof. In the acetylenes outgasser (AG), a bottom stream 27 comprising purified solvent is drawn off and, as shown in the figure, preferably after heat integration with the liquid which is drawn off from the lower combined column region (C) of the dividing wall column, and also with the $C_4$ cut fed to the dividing wall column, stream 1, is recycled into the process as stream 3 and stream 13.

To the acetylenes outgasser (AG) is attached a water scrubber, in which solvent residues are washed out of the outgassed acetylenes stream using reflux and fresh water. At the top of the water scrubber (W) a stream 24 comprising acetylenes is drawn off, condensed in a condenser at the top of the column, partly applied as reflux 25 back to the water scrubber (W) and otherwise discharged from the process as stream 26.

What is claimed is:

1. A process for obtaining crude 1,3-butadiene comprising:
   extractively distilling with a selective solvent the crude 1,3-butadiene in a dividing wall column from a $C_4$ cut comprising $C_4$ acetylenes as secondary components;
   controlling the energy input into the dividing wall column to obtain a bottom stream comprising solvent, $C_4$ acetylenes and an economically acceptable proportion of 1,3-butadiene which is drawn off from the dividing wall column;
   feeding the bottom stream to an acetylenes outgasser;
   wherein the $C_4$ acetylenes are stripped out overhead and purified solvent is obtained as a bottom stream;
   wherein
   the dividing wall column comprises a bottom evaporator,
   a dividing wall is disposed in the longitudinal direction of the dividing wall column to form a first subregion, a second subregion and a lower combined column region having one or more separation stages, and
   the dividing wall column is disposed upstream of an extractive wash column.

2. The process according to claim 1, wherein the economically acceptable proportion of 1,3-butadiene in the bottom stream of the dividing wall column is in a range of from 0.1 to 2 times the proportion of $C_4$ acetylenes in the bottom stream of the dividing wall column.

3. The process according to claim 2, wherein the economically acceptable proportion of 1,3-butadiene in the bottom stream of the dividing wall column is 0.3 times the proportion of $C_4$ acetylenes in the bottom stream of the dividing wall column.

4. The process according to claim 1, further comprising:
   utilizing energy of the bottom stream of the dividing wall column for indirect heat exchange with the bottom stream of the acetylenes outgasser and/or with liquid which is drawn off from the one or more separation stages in the lower combined column region of the dividing wall column, and
   selecting the one or more separation stages from which the liquid is drawn off to minimize the energy demand for the dividing wall column.

5. The process according to claim 1, further comprising:
   utilizing a heat content of the bottom stream of the acetylenes outgasser for indirect heat exchange with the liquid which is drawn off from one or more separation stages in the lower combined column region of the dividing wall column, and
   determining the separation stage(s) from which the liquid is drawn off to minimize the energy demand for the dividing wall column, and/or
   utilizing the heat content of the bottom stream for indirect heat exchange with a $C_4$ cut to be separated and fed to the dividing wall column.

6. The process according to claim 1, wherein
   the $C_4$ cut is fed to the first subregion of the dividing wall column,
   the top stream from the first subregion of the dividing wall column is fed to a lower region of the extractive wash column,
   in the extractive wash column, a countercurrent extraction is carried out by charging with a first substream of the selective solvent in the upper region of the extractive wash column,
   the components of the $C_4$ cuts having lower solubility than 1,3-butadiene in the selective solvent are drawn off via the top of the extractive wash column,
   the bottom stream from the extractive wash column is recycled into the upper region of the first subregion of the dividing wall column,
   second substream of the selective solvent is fed to the dividing wall column in the upper region of the second subregion,
   the top product from the second subregion of the dividing wall column is drawn off as crude 1,3-butadiene and
   a bottom stream comprising solvent, the $C_4$ acetylenes, and an economically acceptable proportion of 1,3-butadiene, is drawn off from the lower combined column region of the dividing wall column,
   the bottom stream is fed to the acetylenes outgasser in which the $C_4$ acetylenes are stripped out overhead and purified solventobtained as the bottom stream is recycled into the process.

7. The process according to claim 6, wherein the $C_4$ cut is fed into the middle region of the first subregion of the dividing wall column.

8. The process according to claim 1, wherein a temperature in the bottom evaporator of the dividing wall column is in the range from 50 to 210° C.,
   a top pressure of the second subregion of the dividing wall column is in the range from 1 to 10 bar absolute and
   a top pressure in the acetylenes outgasser is in the range from 1 bar absolute to a maximum of the bottom pressure in the dividing wall column.

9. The process according to claim 8, wherein the temperature in the bottom evaporator of the dividing wall column is 178° C., and the top pressure of the second subregion of the dividing wall column is in the range from 2 to 5 bar absolute.

10. The process according to claim 9, wherein the top pressure of the second subregion of the dividing wall column is 3.5 bar absolute.

11. The process according to claim 1, wherein the acetylenes outgasser is integrated by construction into the lower combined column region by configuring the number of theoretical plates in the lower combined column region to a correspondingly larger value and incorporating a gas-tight division in the dividing wall column at a point which corresponds to the upper end of the acetylenes outgasser integrated into the lower combined column region.

* * * * *